(12) United States Patent
Gurskis et al.

(10) Patent No.: US 8,323,337 B2
(45) Date of Patent: Dec. 4, 2012

(54) CONNECTION SYSTEMS FOR TWO PIECE PROSTHETIC HEART VALVE ASSEMBLIES AND METHODS FOR MAKING AND USING THEM

(75) Inventors: Donnell W. Gurskis, Belmont, CA (US); Takashi Harry Ino, San Jose, CA (US); Ernest Lane, Huntington Beach, CA (US); Steven R. Bacich, Half Moon Bay, CA (US)

(73) Assignee: Medtronic, Inc., Minneapolis, MN (US)

( * ) Notice: Subject to any disclaimer, the term of this patent is extended or adjusted under 35 U.S.C. 154(b) by 263 days.

(21) Appl. No.: 12/477,861

(22) Filed: Jun. 3, 2009

(65) Prior Publication Data

US 2009/0319038 A1 Dec. 24, 2009

Related U.S. Application Data

(60) Provisional application No. 61/059,252, filed on Jun. 5, 2008.

(51) Int. Cl.
*A61F 2/24* (2006.01)

(52) U.S. Cl. ............ 623/2.41; 623/2.17; 623/2.36; 623/2.38; 623/2.4

(58) Field of Classification Search ............ 623/2.14, 623/2.17, 2.18, 2.36, 2.37, 2.38, 2.4, 2.41, 623/1.24, 1.26, 2.1, 23.68
See application file for complete search history.

(56) References Cited

U.S. PATENT DOCUMENTS

| 3,466,671 A | 9/1969 | Siposs |
| 6,585,766 B1 | 7/2003 | Huynh et al. |
| 2006/0025857 A1 | 2/2006 | Bergheim et al. |
| 2007/0016288 A1* | 1/2007 | Gurskis et al. ............ 623/2.11 |

OTHER PUBLICATIONS

International Search Report and Written Opinion for International PCT Application No. PCT/US2009/046178 mailed Oct. 12, 2009 (15 pages).

* cited by examiner

*Primary Examiner* — Paul Prebilic
*Assistant Examiner* — Leslie Coburn

(57) ABSTRACT

A heart valve assembly includes a prosthesis and a prosthetic valve to replace a preexisting natural or prosthetic heart valve within a biological annulus. The prosthesis includes an annular member, a flexible core at least partially defining a sewing cuff extending radially outwardly from the annular member, a rail ring disposed between the flexible core and the annular member, and a plurality of guide rails extending from the rail ring through respective openings in the flexible core. A fabric covering covers the prosthesis, and the guide rails extend through respective openings in the fabric covering. The prosthetic valve includes a frame including receptacles for receiving respective guide rails. After implanting the prosthesis within a biological annulus, the prosthetic valve is advanced along the guide rails until retention elements on the guide rails engage the receptacles to secure the prosthetic valve relative to the prosthesis.

11 Claims, 14 Drawing Sheets

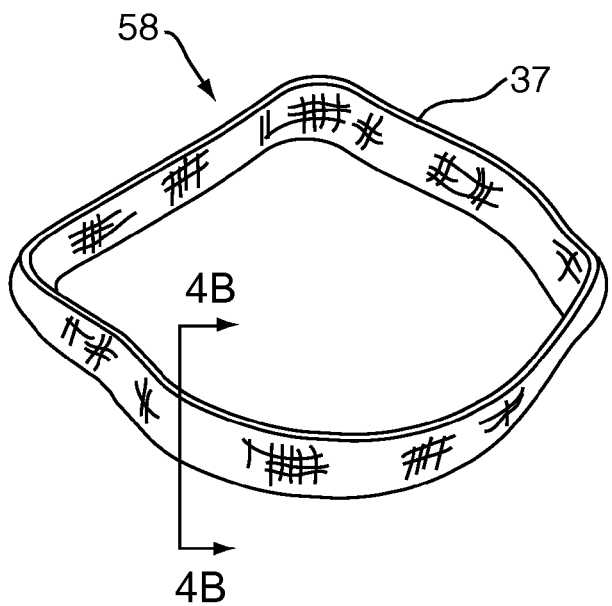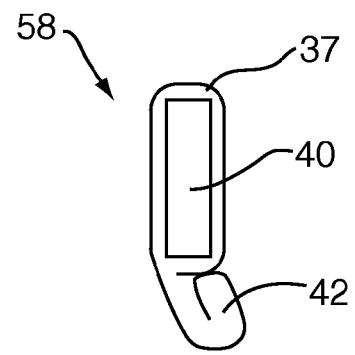
FIG. 4A  FIG. 4B
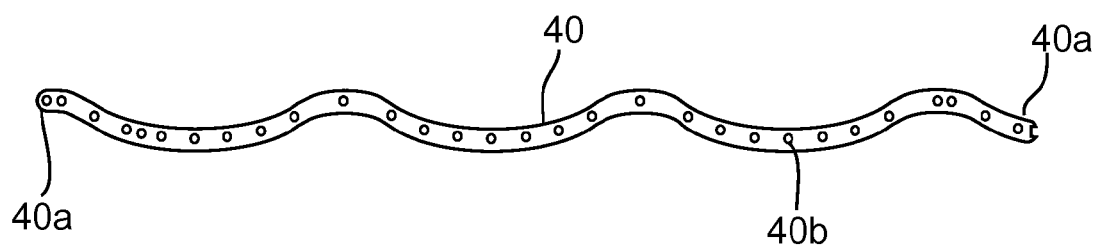
FIG. 4C

CONNECTION SYSTEMS FOR TWO PIECE PROSTHETIC HEART VALVE ASSEMBLIES AND METHODS FOR MAKING AND USING THEM

RELATED APPLICATION DATA

This application claims benefit of co-pending provisional application Ser. No. 61/059,252, filed Jun. 5, 2008, the entire disclosure of which is expressly incorporated by reference herein.

FIELD OF THE INVENTION

The present invention relates generally to heart valves that may be implanted within a patient, and, more particularly, to connection systems for multiple component heart valves that may be assembled together, and to methods for making and using them.

BACKGROUND

Prosthetic heart valves can replace defective human valves in patients. For example, one piece valves have been suggested that include sewing rings or suture cuffs that are attached to and extend around the outer circumference of a prosthetic valve. In addition, multiple component valves have also been suggested that include a sewing ring that is separate from a valve component. The sewing rings of either type of prosthetic valve can be tedious and time consuming to secure within a target site, i.e., within an annulus of a heart where a natural heart valve has been removed.

For example, to implant a sewing ring within an annulus of a heart, between twelve and twenty sutures may be secured initially to tissue surrounding the annulus. The sewing ring and/or the entire prosthetic valve may then be advanced or "parachuted" down the sutures into the annulus. Knots may then be tied with the sutures to secure the sewing ring within the annulus, whereupon the sutures may be cut. Consequently, this procedure can be very complicated, requiring management and manipulation of many sutures. The complexity of the procedure also provides a greater opportunity for mistakes and requires a patient to be on cardiopulmonary bypass for a lengthy period of time.

Because the annulus of the heart may not match the circular cross-section of the sewing ring and/or prosthetic valve, the prosthetic valve may not fit optimally within the annulus. As a result, natural blood hemodynamics through and around the valve may be impaired, resulting in clotting, possible emboli production, and/or eventual calcification of the valve structure.

To address this concern, flexible sewing rings have been suggested for use with multiple component valves. The sewing ring may be implanted within the annulus, e.g., using the procedure described above, i.e., parachuted down an arrangement of sutures. The sewing ring may conform at least partially to the anatomy of the annulus. Alternatively, instead of using sutures, it has also been suggested to drive staples through the sewing ring into the surrounding tissue to secure the sewing ring.

When a mechanical or prosthetic valve is then attached to the sewing ring, however, the valve and sewing ring may not mate together effectively, e.g., if the shape of the sewing ring has been distorted to conform to the annulus, which may also impair natural blood hemodynamics, create leaks, and/or otherwise impair performance of the prosthetic valve.

SUMMARY OF THE INVENTION

The present invention is directed to heart valves that may be implanted within a patient, and, more particularly, to multiple component heart valve assemblies that may be assembled together, and to apparatus and methods for making and implanting them.

In accordance with one embodiment, a prosthesis is provided for receiving a prosthetic valve to replace a preexisting natural or prosthetic heart valve within a biological annulus adjacent a sinus cavity. The prosthesis may include an annular member implantable within the biological annulus, a sewing cuff extending outwardly from the annular member, e.g., above a plane of the annular member, a rail ring positioned within the sewing cuff and/or adjacent the annular member, and a plurality of guide rails including first ends coupled to the rail ring and second free ends. Each of the guide rails may include one or more retention elements for securing a prosthetic valve relative to the prosthesis. Optionally, the guide rails may include weakened regions, e.g., above the one or more retention elements, to facilitate severing the guide rails after securing a prosthetic valve to the prosthesis. In addition or alternatively, the prosthesis may include a flexible skirt or baleen element extending outwardly from the annular member, e.g., below the plane of the annular member.

In accordance with another embodiment, a prosthesis is provided for receiving a prosthetic valve that includes an annular member implantable within a biological annulus, a rail ring disposed adjacent the annular member, a plurality of guide rails including first ends coupled to the rail ring and second free ends, and a fabric covering the annular member and rail ring. For example, each of the guide rails may extend from the rail ring through respective openings in the fabric covering. Each of the guide rails may include one or more retention elements for securing a prosthetic valve relative to the prosthesis. Optionally, the prosthesis may include a sewing cuff extending outwardly from the annular member, e.g., above a plane of the annular member. The sewing cuff may be formed at least partially from the fabric covering and/or may include a flexible core. In one embodiment, the rail ring may be disposed between the flexible core and the annular member, and the flexible core may include a plurality of openings receiving the guide rails therethrough.

In accordance with yet another embodiment, a heart valve assembly is provided for implantation within a biological annulus. The heart valve assembly may include an annular prosthesis that includes an annular member sized for introduction into the biological annulus, a sewing cuff, a rail ring, and a plurality of guide rails including one end attached to the rail ring. The heart valve assembly may also include a prosthetic valve that may include an annular frame and receptacles for receiving the guide rails, e.g., for guiding the prosthetic valve along the guide rails towards the annular prosthesis. The annular prosthesis and/or prosthetic valve may include one or more cooperating connectors for securing the prosthetic valve relative to the annular prosthesis. For example, the prosthetic valve may include a plurality of receptacles including detents or other elements for receiving corresponding retention elements or other connectors on the guide rails for securing the prosthetic valve relative to the annular prosthesis.

In accordance with still another embodiment, a heart valve assembly is provided that includes a first prosthesis and a second valve prosthesis. The first prosthesis may include an annular member implantable within a biological annulus, a sewing cuff including a flexible core extending outwardly from above the annular member, a rail ring positioned between the annular member and the flexible core, and a plurality of guide rails attached to the rail ring. The second valve prosthesis may include an annular frame and receptacles for receiving respective guide rails such that the second prosthesis may be directed along the guide rails towards the first prosthesis. Retention elements may be provided on the guide rails for engaging respective detents in the receptacles for securing the second prosthesis relative to the first prosthesis.

In accordance with yet another embodiment, a heart valve assembly is provided that includes a first prosthesis including an annular member implantable within a biological annulus, a rail ring, and a flexible skirt or baleen element extending radially outwardly along a lower edge of the annular member. A plurality of guide rails may extend from the rail ring. The assembly may also include a second valve prosthesis including an annular frame and receptacles for receiving respective guide rails such that the second prosthesis may be directed along the guide rails towards the first prosthesis. Additionally, the assembly many include means for securing the second prosthesis relative to the first prosthesis.

In accordance with another embodiment, a method is provided for making an annular prosthesis for implanting a valve prosthesis that includes forming a rail ring including a plurality of guide rails extending therefrom, forming an annular member, and substantially surrounding the rail ring and annular member with a fabric covering such that the rail ring and annular member surround a central passage. Openings may be formed in the fabric covering to accommodate extending the guide rails from the rail ring therethrough. The annular member may be formed by rolling a sheet into a band, and then the annular member and rail ring may be secured to one another, e.g., such that the rail ring is disposed concentrically adjacent the annular member. Optionally, a flexible core may be formed and disposed adjacent the rail ring, e.g., before surrounding the rail ring with the fabric covering. For example, the flexible core may be placed above the rail ring such that the rail ring is disposed between the flexible core and the annular member. The flexible core may have a larger cross-section than the rail ring and annular member such that, once received within the fabric covering, the flexible core at least partially defines a sewing cuff extending radially from the annular member. Optionally, the flexible core may include a plurality of openings therethrough and the guide rails may be extended through respective openings before completing surrounding the rail ring and flexible core with the fabric covering.

In accordance with yet another embodiment, a method is provided for implanting a prosthetic heart valve assembly within a biological annulus. An annular prosthesis is provided that includes an annular member and a plurality of guide rails extending from the annular member. The annular prosthesis may be directed towards the biological annulus, e.g., until the annular member is introduced into the biological annulus. One or more connectors, e.g., sutures, clips, and the like, may be directed through a portion of the annular prosthesis, e.g., through a sewing cuff or skirt extending radially from the annular member, to secure the annular member within the biological annulus. A valve prosthesis, e.g., a mechanical or bioprosthetic valve, may be advanced over the guide rails, and secured relative to the annular member. For example, the valve prosthesis may include a plurality of receptacles for receiving respective guide rails therethrough, such that the valve prosthesis is advanced down the guide rails towards the annular prosthesis. The guide rails may include one or more retention elements, e.g., buttons, detents, beveled surfaces, and the like, that may be received in the receptacles for securing the valve prosthesis to or adjacent the annular prosthesis. The guide rails may then be removed, e.g., by severing the guide rails above the receptacles and retention elements, leaving the valve prosthesis secured to annular prosthesis adjacent the biological annulus.

In accordance with still another embodiment, a method is provided for implanting a heart valve assembly in a biological annulus that includes inserting a first annular prosthesis into the biological annulus, the first prosthesis comprising a plurality of guide rails extending therefrom and each of the plurality of guide rails comprising at least one retention element; securing the first prosthesis to tissue surrounding the biological annulus; directing free ends of the guide rails through respective receptacles on a second valve prosthesis; advancing the second prosthesis along the guide rails towards the first prosthesis until a tapered lower surface of the receptacles engages a tapered upper surface of the retention elements; deflecting spring elements of the receptacles outward by sliding the tapered lower surface of the receptacles along the tapered upper surface of the retention elements; and securing the second prosthesis relative to the first prosthesis by returning the spring elements inwardly, thereby locking detents on the spring elements into a position below the retention elements.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 4A is a perspective view of a collar that may be attached to the gasket member of FIGS. 1A-1D.

FIG. 4B is a cross-sectional view of the collar taken along line 4B-4B in FIG. 4A.

FIG. 4C is a side view of a flat band that may provide a core for the collar of FIGS. 4A and 4B.

DETAILED DESCRIPTION OF THE EXEMPLARY EMBODIMENTS

Figure 1A:
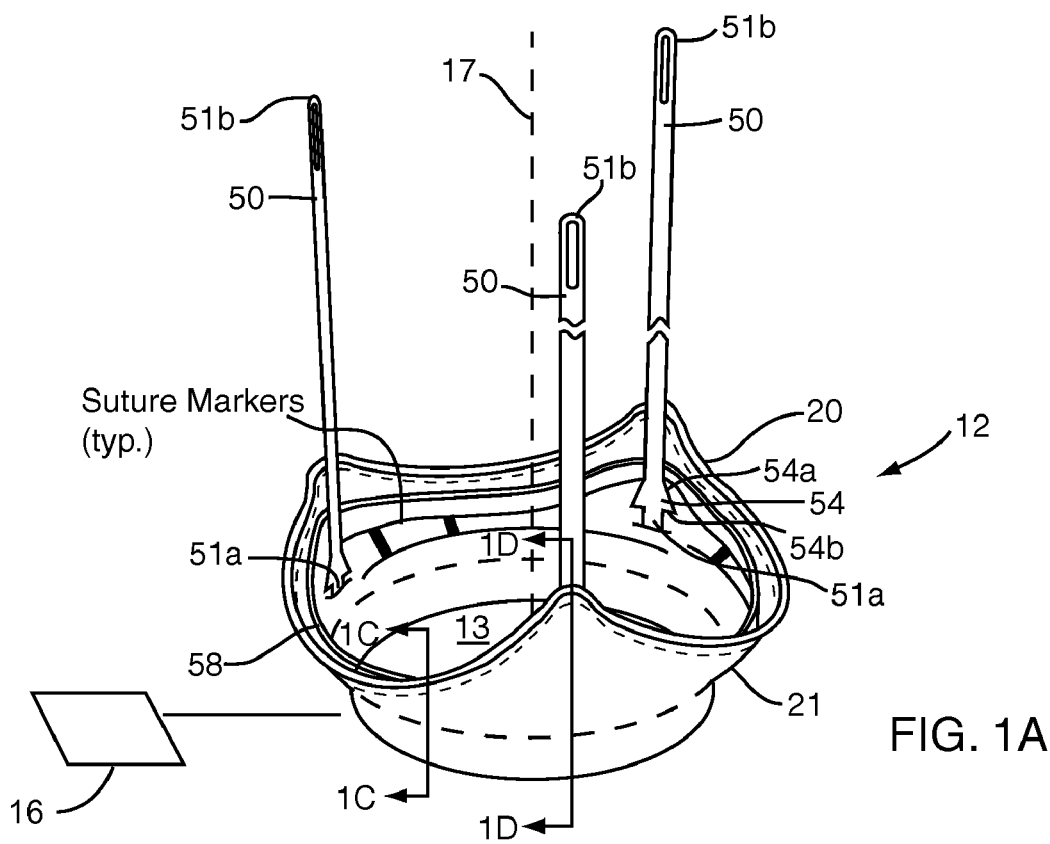
FIG. 1A is a perspective view of an exemplary embodiment of a gasket member for a two piece heart valve assembly.
Figure 1B:
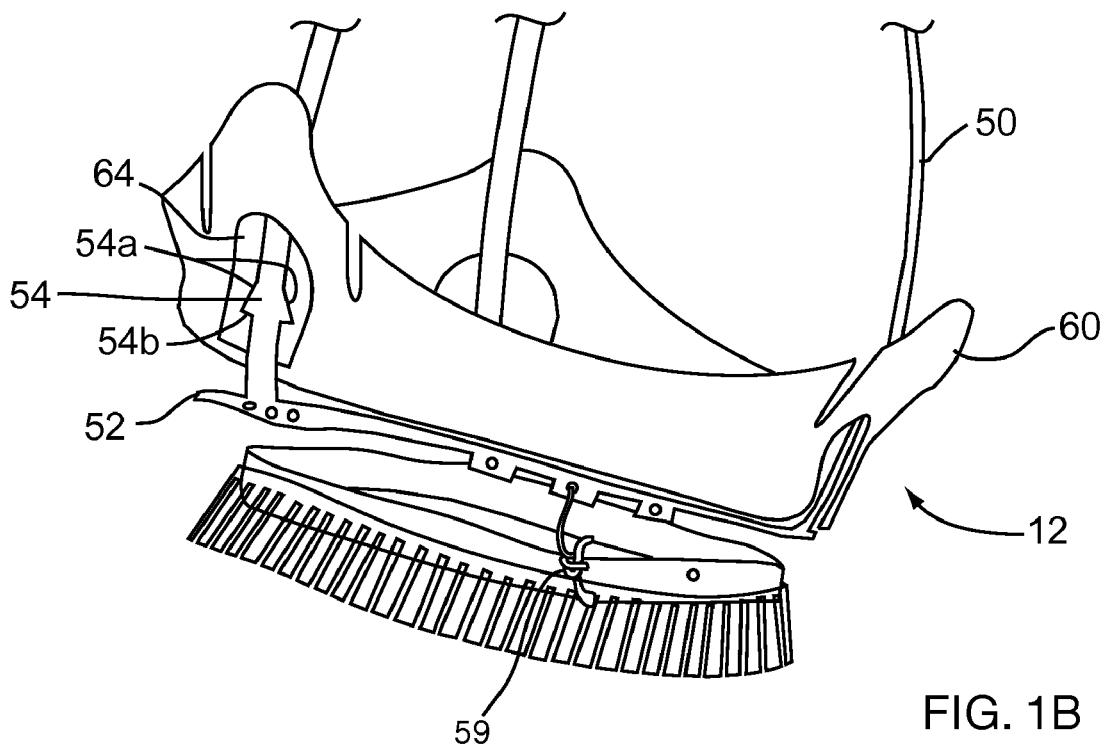
FIG. 1B is a perspective view of the gasket member of FIG. 1A with a fabric covering removed to show internal components of the gasket member.
Figure 1C:
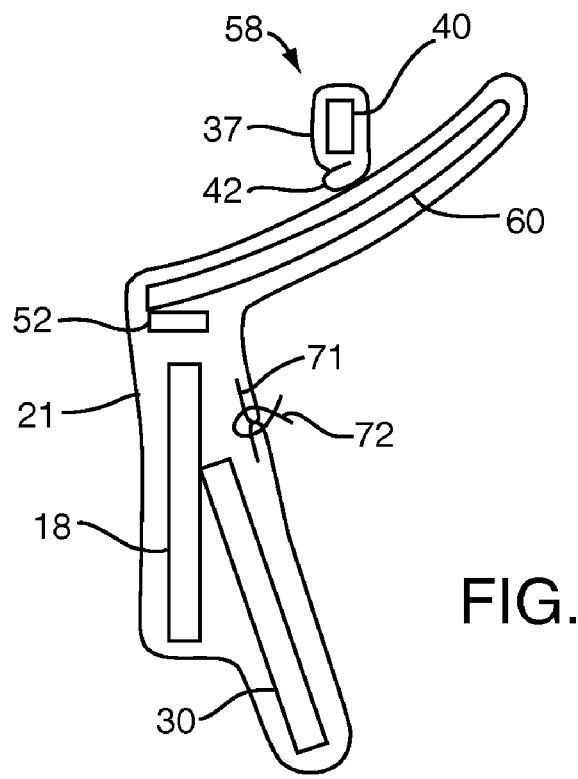
FIGS. 1C and 1D are cross-sectional views of the gasket member taken along lines 1C-1C and 1D-1D in FIG. 1A, respectively.
Figure 1D:
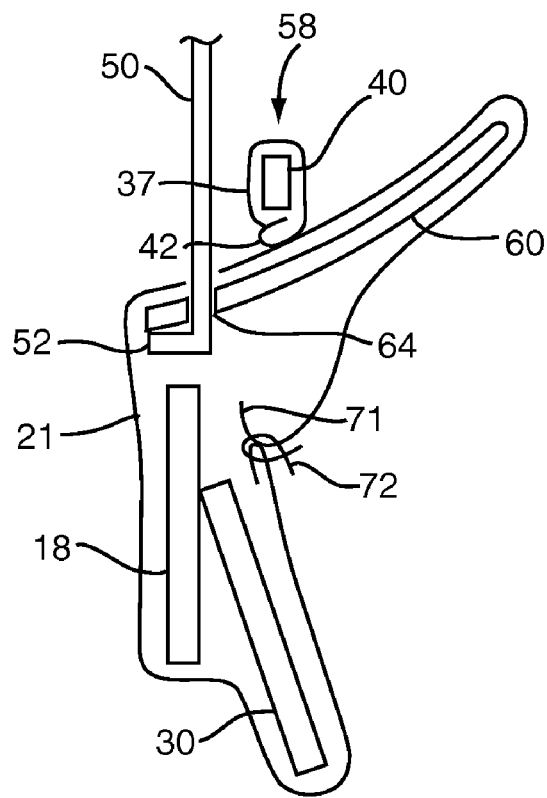

Turning to the drawings, FIGS. 1A-1D show an exemplary embodiment of a gasket member 12 including a plurality of internal annular components substantially received within or surrounded by a fabric covering 21 to define a passage 13 therethrough generally along a central longitudinal axis 17, and a plurality of elongate guide rails 50 extending therefrom, as shown in FIG. 1A. As best seen in FIG. 1B, the gasket member 12 generally includes an annular ring 18, a flexible baleen element or skirt 30, a sewing cuff or ring 20 including a flexible core 60, and a rail ring 52 including the guide rails 50 extending therefrom, as described further below. As shown in FIGS. 1B-1D, the fabric covering 21 may be provided on or around one or more components of the gasket member 12, e.g., over the annular ring 18, the core 60 of the sewing cuff 20, the skirt 30, and/or the rail ring 52, also as described further below.

In one embodiment, the annular ring 18 may have a generally circular shape disposed around the longitudinal axis 17 and generally parallel to plane 16. Optionally, the annular ring 18 may include an undulating shape, including portions that extend axially above and/or below the plane 16. Alternatively, the annular ring 18 may have a multi-lobular shape about the circumference, including lobes separated by scallops or cusps (not shown). In addition or alternatively, the annular ring 18 may be expandable and/or contractible such that the diameter (or other cross-section if the annular ring 18 is noncircular) may be adjusted, e.g., based upon the anatomy of the patient encountered during a procedure. In one embodiment, the annular ring 18 may be biased to expand to a predetermined diameter. Thus, the annular ring 18 may be contracted radially to a smaller diameter, e.g., to facilitate delivery into an annulus, yet may be resiliently expandable to reshape and/or dilate tissue surrounding the annulus and/or to facilitate securing the gasket member 12 within the annulus.

The annular ring 18 may be formed from an elastic or superelastic material, such as Nitinol, stainless steel, plastic, and the like. For example, the annular ring 18 may be cut from a flat sheet of base material having a desired thickness for the annular ring 18, e.g., between about 0.1-0.5 millimeters, for example, by laser cutting, mechanical cutting, and the like. Thus, as best seen in FIG. 2E, the annular ring 18 may be initially formed as a long band of material, having a width "W" corresponding to the desired width of the annular ring 18, e.g., between about 1.5-2.5 millimeters, and a length "L" corresponding to a desired circumference of the annular ring 18, e.g., between about 55-90 millimeters. The band may then be wrapped around a mandrel or otherwise restrained in a generally cylindrical shape with the ends adjacent to one another, and the band may be heat treated or otherwise processed to program the generally cylindrical shape to create the annular ring 18. Alternatively, the band may be held in the generally cylindrical shape by the skirt 30 attached thereto, which arrangement is discussed in further detail below. The generally cylindrical shape may include the ends overlapping one another, spaced apart from one another to provide an open "C" shape, and/or attached to one another.

The skirt 30 may be an annular member including a plurality of flexible fingers 82 extending from a base 80 such that the skirt 30 extends outwardly from the annular ring 18 below a plane of the annular ring 18. The base 80 may have a diameter corresponding substantially to the annular ring 18, e.g., such that the base 80 may be disposed around the annular ring 18. Optionally, the base 80 may be secured to the annular ring 18, e.g., by one or more of an interference fit, adhesive, ultrasonic welding, one or more fasteners such as sutures, and the like. In one embodiment, the base 80 and the annular ring 18 are coupled together at one or more fastener sites located around the circumferences of the base 80 and the annular ring 18. In an exemplary embodiment, shown in FIGS. 2E and 2F, the fastener sites may include sutures 84 secured through corresponding holes 80a, 18a in the base 80 and the annular ring 18. The fingers 82 of the skirt 30 may be biased to extend outwardly from the base 80, thereby defining a frusto-conical shape, as shown in FIG. 1A. For example, the fingers 82 may be biased to an angle of between about one and ten degrees (1-10°) radially outwardly relative to the longitudinal axis 17.

Figure 2:
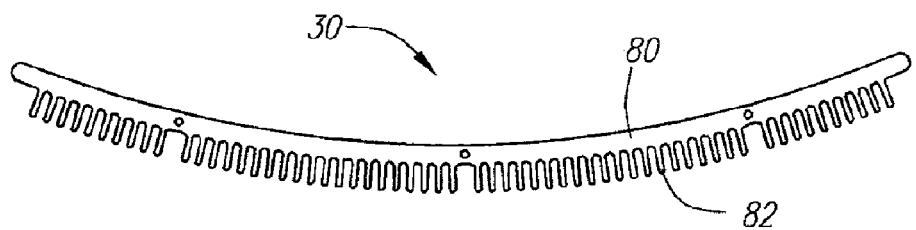
FIGS. 2A-2D are top views of exemplary embodiments of skirts or baleen elements that may be included in the gasket member of FIGS. 1A-1D.
FIG. 2E is a side view of a band for an annular ring of the gasket member of FIGS. 1A-1D having a skirt or baleen element attached thereto.
FIG. 2F is a perspective view of the band and skirt of FIG. 2E attached together and with ends attached together.
Figure 2:
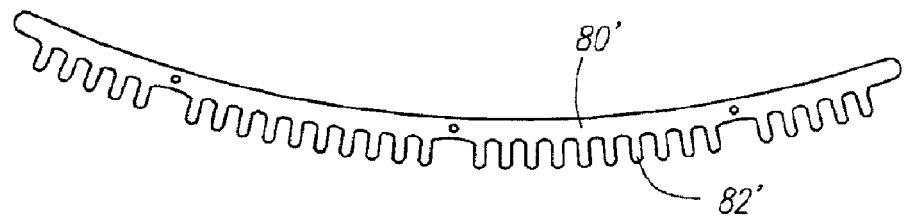
Figure 2:
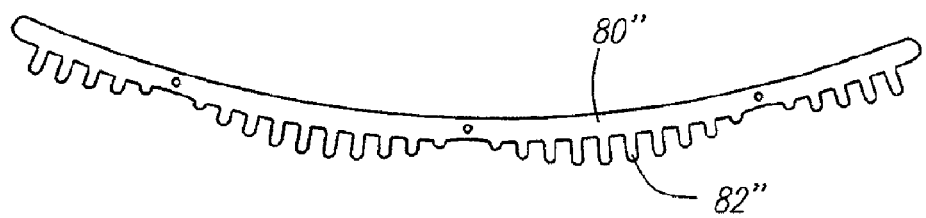
Figure 2:
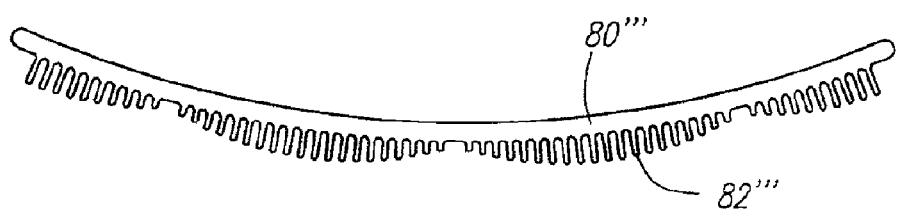
Figure 2E:
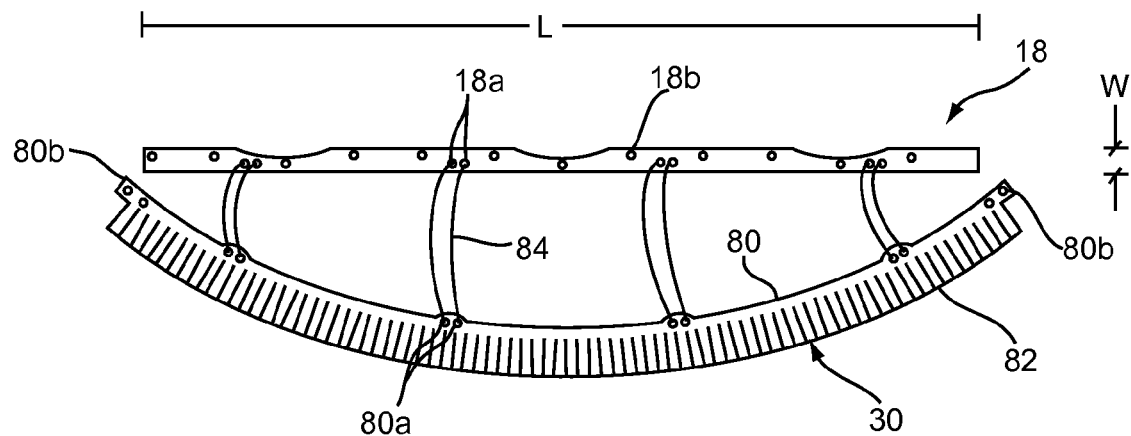

The skirt 30 may be formed from an elongate flat band having the fingers 82 formed therein, such as the skirts 30 shown in FIGS. 2A-2D. In FIGS. 2A and 2B, the fingers 82, 82' have substantially uniform lengths, while in FIGS. 2C and 2D, the fingers 82", 82'" have varying lengths, e.g., defining undulations or lobes, which may correspond to a shape below a biological annulus within which the gasket member 12 may be implanted. In addition, the fingers 82', 82" in FIGS. 2B and 2C are thicker than the fingers 82, 82'" in FIGS. 2A and 2D, which may provide a greater outward bias to enhance billowing the fabric covering 21 outwardly.

The skirt 30 may be formed from a relatively thin band of polyethylene terephthalate ("PET"), polyester or other polymer, an elastic or superelastic alloy, such as Nitinol, and the like, from which the base 80 and fingers 82 may be cut, e.g., by die-cutting, laser-cutting, mechanical cutting, stamping, and the like. In exemplary embodiments, the band (and consequently, the skirt 30) may have a thickness between about 0.002 and 0.010 inch (0.05-0.25 mm). After the skirt 30 is formed, the base 80 may have a width, e.g., between about 0.01-0.08 inch (0.25-2.0 mm), and the fingers 82 may have lengths, e.g., between about 0.01-0.08 inch (0.25-2.0 mm), and widths between about 0.01-0.04 inch (0.25-1.0 mm). As shown in FIGS. 2A-2D, the flat band may define a curve, e.g., such that when the band is rolled and its ends attached together, the base 80 and/or fingers 82 may be tapered to define a frusto-conical shape, as described above. The ends of the band may be attached together by ultrasonic welding, adhesives, fasteners such as sutures, and the like. In one embodiment, the ends of the band are attached together, e.g., by tying sutures through tabs 80*b* (shown in FIG. 2E), and the ends are not attached to the ends of the band of the annular ring 18. When the skirt 30 and the annular ring 18 are both formed from long bands of material, as described above, the bands may be coupled together at one or more fastener sites along the length of the bands (between the ends of the bands), and then the bands may be maintained in a generally cylindrical shape by attaching the ends of the base 80 together, e.g., at tabs 80*b*.

Alternatively, the skirt 30 may be molded or otherwise formed as a continuous piece in the desired frusto-conical shape and attached to the annular ring 18. For example, the skirt 30 may be molded directly around the annular ring 18 or the skirt 30 may be molded separately from the annular ring 18 and then attached to the annular ring 18 as described above.

Returning to FIGS. 1A and 1B, the sewing cuff 20 generally extends radially outwardly from the annular ring 18, e.g., from an upper portion of the annular ring 18, as best seen in FIG. 1A. The sewing cuff 20 has a multiple-lobular outer shape, e.g., defining three lobes corresponding to the commissures of the sinus region above an aortic valve of a heart (not shown). The flexible core 60 of the sewing cuff 20 may be an annular body having a generally frusto-conical shape, e.g., having a narrower lower diameter or other cross-section adjacent the annular ring 18 and extending radially upwardly and away from the longitudinal axis 17, thereby defining the multiple-lobular outer shape. The core 60 may be attached, either directly or with intervening elements (discussed further below), to the upper portion of the annular ring 18. Alternatively, the core 60 may be eliminated and the sewing cuff 20 may simply be formed from one or more layers of fabric or other material, e.g., adjacent to or covering at least a portion of the annular ring 18.

Figure 3A:
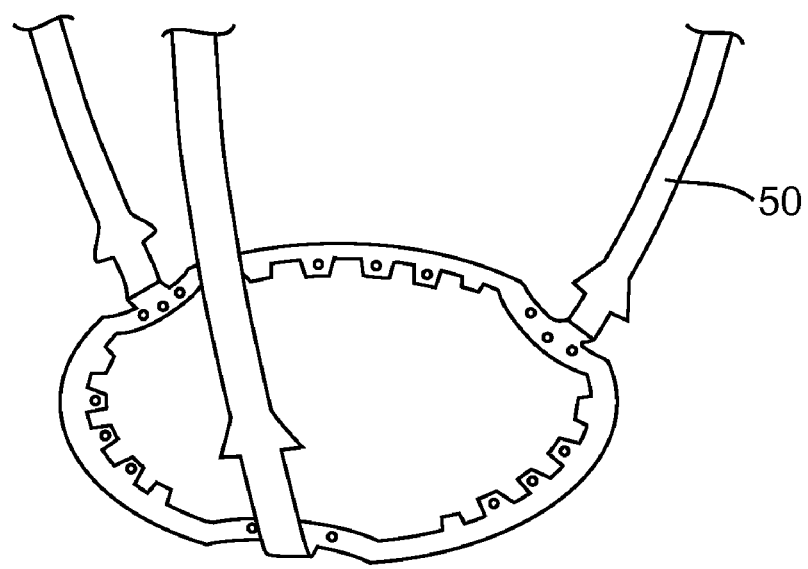
FIG. 3A is a perspective view of a rail ring including guide rails that may be included in the gasket member of FIGS. 1A-1D.
Figure 3B:
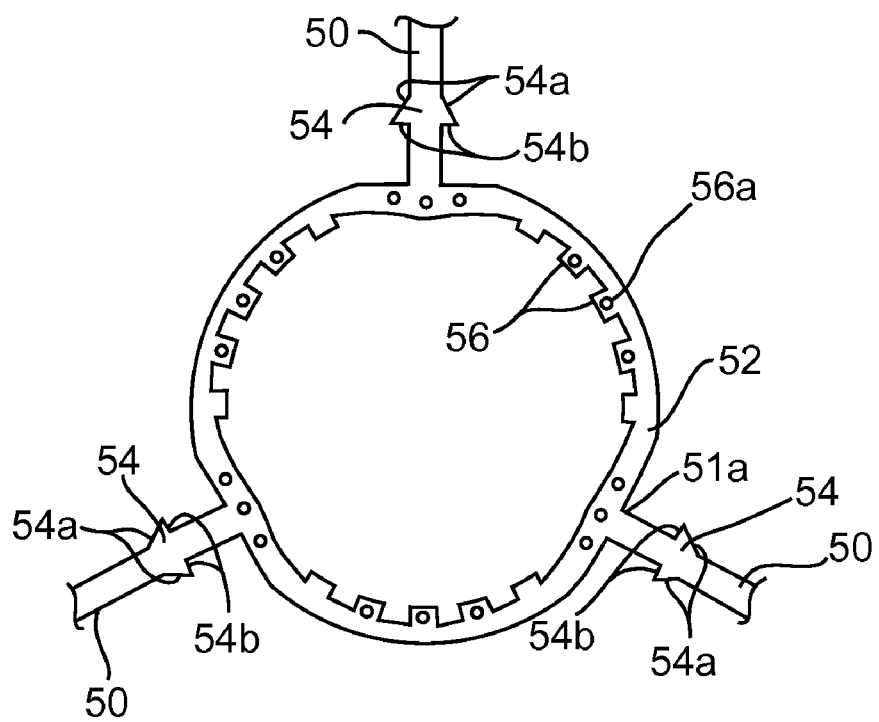
FIG. 3B is a top view of the rail ring and guide rails of FIG. 3A in a flattened position.
Figure 3C:
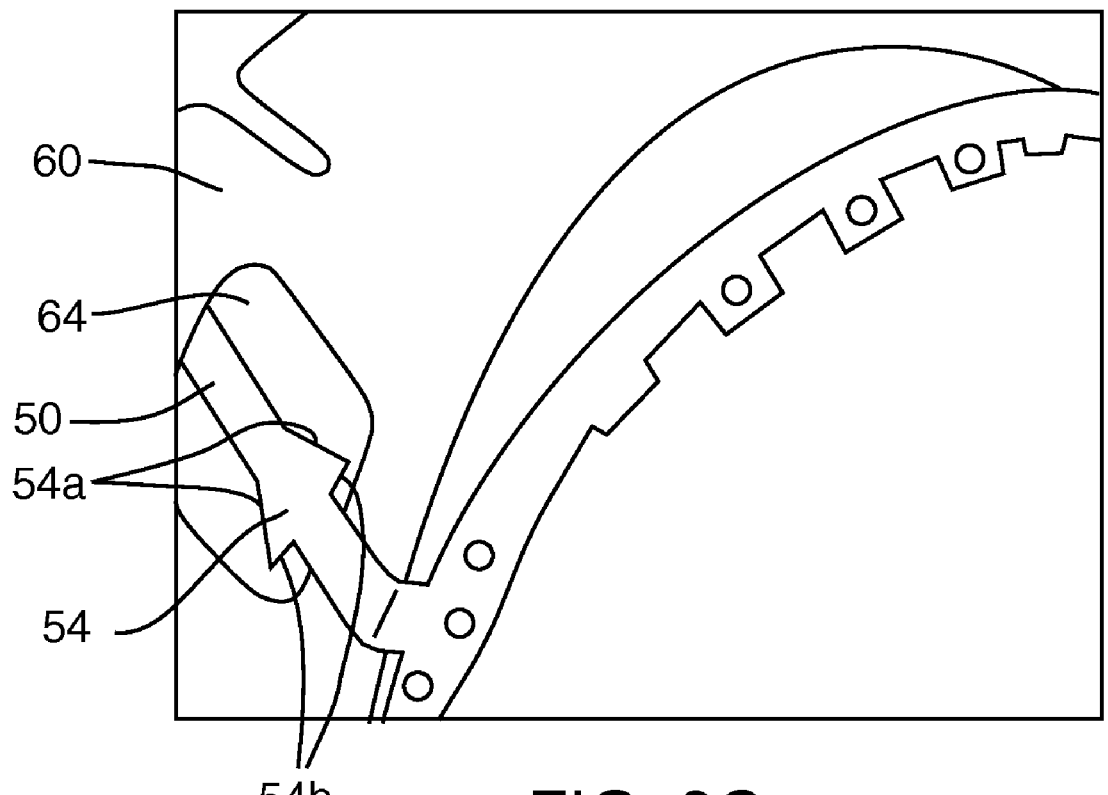
FIG. 3C is a perspective view of the rail ring of FIG. 3A with a guide rail disposed through an opening adjacent to a core of a sewing cuff.
Figure 3D:
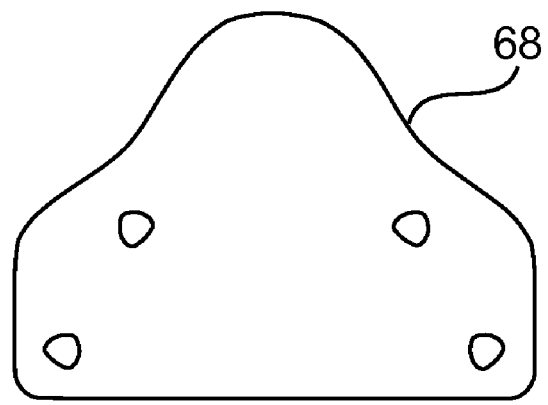
FIG. 3D is a detail of a commissure support that may be attached to a core of a sewing cuff.
Figure 3E:
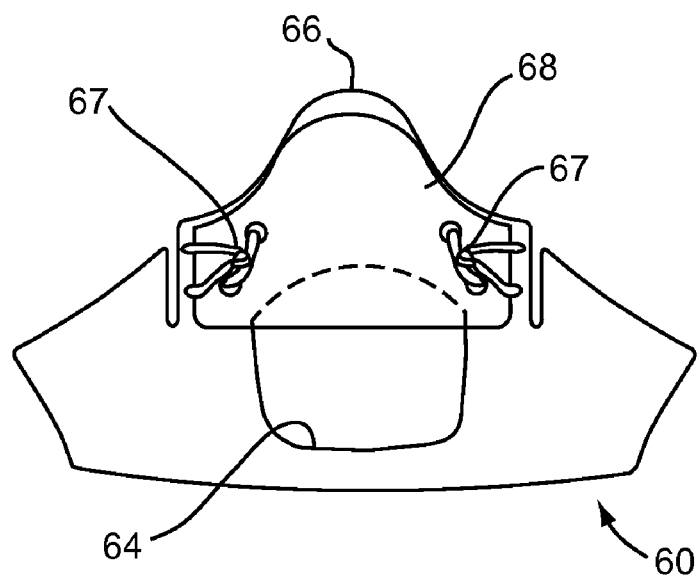
FIG. 3E is a detail showing the commissure support of FIG. 3D being attached to a core of a sewing cuff.

As shown in FIGS. 1B and 3C, the core 60 may include a plurality of holes 64 for receiving the guide rails 50 therethrough, as described further below. The holes 64 may be spaced apart around the circumference of the core 60, e.g., adjacent the lobes 66 of the core 60. Optionally, additional support panels may be provided adjacent the holes 64 and/or lobes 66. For example, as shown in FIGS. 3D and 3E, commissure supports 68 may be attached above the holes 64, e.g., using sutures 67 or other connectors, bonding with adhesive, sonic welding, and the like.

The material of the core 60, commissure supports 66 and/or other components of the sewing cuff 20 may be substantially flexible, e.g., manufactured in a desired annular shape (such as those just described), yet easily deformed, e.g., deflected, stretched, and/or compressed. The core 60 may be sufficiently flexible to be "floppy," i.e., such that the sewing cuff 20 conforms easily and/or substantially based upon the particular anatomy and/or implantation arrangements encountered during implantation. Thus, when the sewing cuff 20 is placed above or within a tissue annulus within a patient's heart, the core 60 may conform to the surrounding anatomy and/or may deform when a valve member (discussed below) is secured to the gasket member 12, e.g. to enhance sealing between the valve member and the gasket member 12 without applying substantial force on the contacted tissue.

For example, when implanted within or above a tissue annulus, the core 60 may lie against the surrounding tissue, thereby changing its shape from its original generally circular or multi-lobular shape, changing the shape of any undulations, and/or changing the angle of the original taper. Thus, the core 60 may become more vertical or inward when the lobes 66 lie against the commissures (not shown) of the tissue annulus, and become more horizontal or outward when regions between the lobes 66 lie within the sinuses above and between the commissures (also not shown). When fasteners (not shown) are driven through the sewing cuff 20, the core 60 may resiliently stretch or compress to distribute forces from the fasteners more evenly, which may reduce bunching of the sewing cuff 20 or other distortions that may otherwise result in leakage.

Figure 2F:
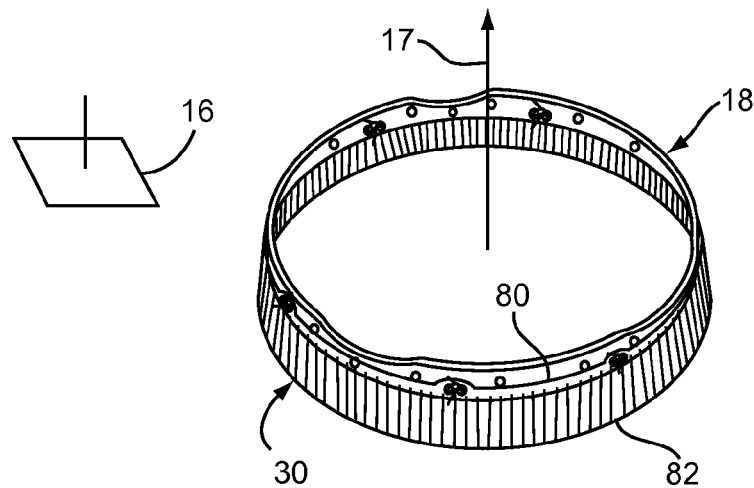

Exemplary materials for the core 60 and commissure supports 64 include silicone or other elastomeric materials, foam, fabric, felt, polymers, and the like. The materials may be molded or otherwise formed into the core 60, e.g., using molding, extrusion, machining, cutting, or other manufacturing procedures. For example, the core 60 may be injection molded or otherwise formed in its annular shape including the lobes 66 and holes 64, as shown in FIGS. 2E and 2F. Additional information on flexible cores or other constructions of the sewing cuff 20 may be found in U.S. Publication No. US 2006/0195184, filed as Ser. No. 11/069,081 on Feb. 28, 2005, the entire disclosure of which is expressly incorporated by reference herein.

Returning to FIGS. 1A and 1B with further reference to FIGS. 3A-3C, the rail ring 52 may be an annular sheet including the guide rails 50 extending therefrom. The rail ring 52 may have a substantially circular shape, e.g., similar to the diameter of the annular ring 18, may have a multiple-lobular shape, e.g., similar to the core 60 of the sewing ring 20, or may have an intermediate shape between the two. In addition, the rail ring 52 may include a plurality of tabs 56 or other connectors, e.g., for connecting the rail ring 52 to the annular ring 18 and/or other components of the gasket member 12 (not shown), as described further below.

The guide rails 50 may include one or more unidirectional or bidirectional retention elements 54, e.g., locking beads, tabs, ratchets, detents, and the like. The retention elements 54 may be integrally formed on the guide rails 50, e.g., at the time the guide rails 50 are formed, or may be separate elements (made from the same or different materials than the guide rails 50) that are bonded, fused, or otherwise attached to the guide rails 50 at predetermined locations. Alternatively, the guide rails 50 may be flat bands, e.g., formed from plastic or other material, and may have the retention elements 54 formed therein or attached thereto, as described elsewhere herein.

As shown in FIGS. 3A-3C, the retention elements 54 on the guide rails 50 may include tapered proximal edges 54*a* and substantially blunt distal edges 54*b*. The proximal edges 54*a* may provide a substantially smooth transition allowing a valve member (discussed below) to be passed distally over the retention elements 54. The distal edges 54*b* may provide locks that prevent the valve member from being passed proximally back over the retention elements 54, similar to a ratchet or detent, as described further below. In alternative embodiments, the retention elements 54 on the guide rails 50 may include knots (not shown) tied onto the guide rails 50 and/or beads (also not shown) formed on the guide rails 50 at predetermined locations. Although only one retention element 54 is shown on each guide rail 50, optionally, multiple retention elements 54 may be provided spaced apart from one another along each guide rail 50.

Optionally, the guide rails 50 may include weakened regions (not shown), e.g., above the retention elements 54 or otherwise disposed a predetermined distance from the first ends 51*a*. When a predetermined tension is applied to the guide rails 50, the weakened regions may automatically fail, thereby separating the first ends 51*a* from the remainder of the guide rails 50, which may then be removed from the patient's body. This option may eliminate the need to introduce scissors or other cutting tools into the patient to cut the guide rails 50. If desired, e.g., in an acute emergency situation or if a valve member (not shown) is being replaced, the remaining portions of the guide rails 50 may be cut below the retention elements 54 to release the valve member, allowing the valve member to be removed from the gasket member 12 and/or patient's body.

The weakened regions may include a notch, slit, groove, cut, necking, thinning, score mark, and/or narrowing on either or both edges of the guide rails 50, across the entire width of the guide rails 50, and/or axially or diagonally along the length of the guide rails 50.

Any number of guide rails 30 may be provided on the rail ring 52. For example, for a prosthesis for an aortic valve having three commissures, three guide rails may be provided. In one embodiment, first ends 51a of the guide rails 50 may be integrally formed with the rail ring 52, as best seen in FIGS. 3A and 3B, and second ends 51b of the guide rails 50 may remain free, as best seen in FIG. 1A. Alternatively, the guide rails 50 may be formed separately from the rail ring 52, and the first ends 51a of the guide rails 50 may be attached to the rail ring 52, e.g., by bonding with adhesive, sonic welding, using sutures or other connectors, and the like (not shown). In this alternative, each guide rail may be attached to the gasket member 12, e.g., at spaced apart intervals from one another. For example, the guide rails may be provided at circumferential locations on the gasket member 12 that are aligned with commissures on a valve member and/or a biological annulus (not shown) into which the gasket member 12 is to be implanted.

In an exemplary embodiment, the guide rails 50 and the rail ring 52 may be formed as a unitary piece, e.g., from PET, polyester or other plastic, an elastic or superelastic alloy, such as Nitinol, and the like, by molding, extruding, cutting, or other manufacturing procedures. The guide rails 50 may be formed from materials having sufficient column strength such that the guide rails 50 are substantially self-supporting, e.g., do not collapse under their own weight, yet are sufficiently flexible to be manipulated during use, e.g., to direct them out of the way when desired.

For example, a flat sheet of PET or other plastic may be provided, and the guide rails 50, rail ring 52, and tabs 56 may be formed from the flat sheet, as shown in FIG. 3C, e.g., by laser cutting, die cutting, stamping, and the like. The guide rails 50 and the tabs 56 may be subsequently bent into the desired orientations, e.g., as shown in FIGS. 1A and 3A. Desired features, such as those described below, may be formed into the guide rails 50 and the rail ring 52, e.g., by machining, punching, etching, mechanical or laser cutting, drilling, or otherwise removing material from the guide rails 50 and the rail ring 52. Alternatively, the desired features may be formed originally in the guide rails 50 and the rail ring 52, e.g., by injection molding.

The guide rails 50 are spaced apart from one another about a periphery of the rail ring 52 and may extend transversely relative to the rail ring 52, e.g., generally parallel to the longitudinal axis 17 or otherwise upwardly above a plane defined by the rail ring 52, as best seen in FIG. 3A. For example, if the guide rails 50 are integrally formed with the rail ring 52, the guide rails 50 may initially lie within the plane of the rail ring 52, but may be bent, broken, or otherwise deformed to extend transversely relative to the rail ring 52.

As shown in FIGS. 1A and 3B, after assembly, the guide rails 50 may extend through the holes 64 in the core 60 of the sewing cuff 20. For example, the core 60 may be positioned above the rail ring 52, i.e., with the rail ring 52 between the core 60 and the annular ring 18 as best seen in FIG. 1B, and the guide rails 50 may be inserted through the holes 64 in the core 60 so that the second free ends 51b of the guide rails 50 extend above the plane of the annular ring 18.

Figure 3F:
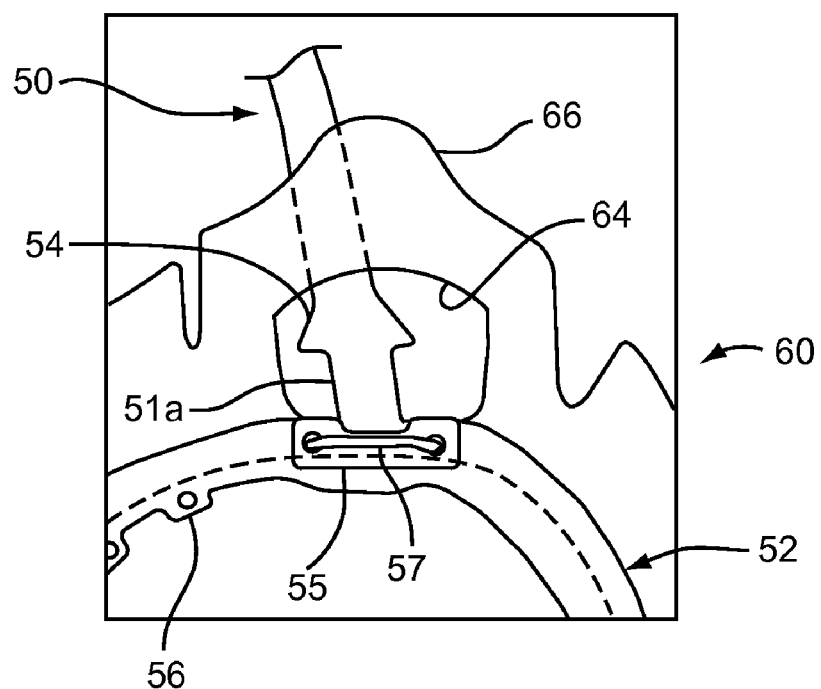
FIG. 3F is a detail of a stress diffusor being attached to a guide rail and core of a sewing cuff.

Optionally, the rail ring 52 and/or guide rails 50 may be secured relative to the core 60, e.g., to stabilize or otherwise maintain the relative position of the guide rails 50 relative to the core 60. For example, as shown in FIG. 3F, after a guide rail 50 is inserted through a hole 64 in the core 60, a panel 55 of material may be secured to the core 60 and rail ring 52 over the first end 51a of each guide rail 50. The panel 55 may be a relatively small plastic sheet, e.g., silicone, PET, or other material similar to the rail ring 52 and/or core 60. The panel 55 may be attached to the core 60 and rail ring 52 using one or more sutures 57 or other connectors, such as staples, clips, and the like, by bonding with adhesive, sonic welding and the like. As shown, the guide rails 50 may be free to slide between the core 60 and the panel 55, e.g., a short distance up or down limited by the rail ring 52 or the retention elements 54 abutting the core 60.

As shown in FIG. 1A, the outer diameters of the rail ring 52 and the annular ring 18 may be substantially the same and the rail ring 52 may be positioned as an intervening element between the core 60 and the upper edge of the annular ring 18. In order to attach the rail ring 52 to the annular ring 18, the rail ring 52 may be fused along the upper edge of the annular ring 18, e.g., by softening or melting the rail ring 52 material, or otherwise attached or secured using one or more fasteners, such as sutures, clips, and the like, bonding with adhesive, sonic welding, and the like. Alternatively, the rail ring 52 may be butted against the annular ring 18 or otherwise disposed adjacent the upper edge of the annular ring 18, and held in relative position by the fabric covering 21.

In one embodiment, with reference to FIGS. 1B, 2E, and 3B, the tabs 56 on the rail ring 52 may be used for facilitating connection between the rail ring 52 and the annular ring 18. One or more of the tabs 56 may be bent downwardly or otherwise may extend below the plane of the rail ring 52, e.g., at an angle, as shown in FIG. 1B. For example, one or more of the tabs 56 may extend below the plane of the rail ring 52 at an angle of about sixty degrees (60°). The rail ring 52 and the annular ring 18 may be held in relative position by one or more sutures 59 or other fasteners delivered through the one or more angled tabs 56 and the annular ring 18. To facilitate suture delivery, one or more openings 56a may be provided in the tabs 56 (see FIG. 3B) and one or more corresponding openings 18b may be provided in the annular ring 18 (see FIG. 2E) and the sutures 59 may be delivered through the corresponding sets of openings 56a, 18b, such as the suture 59 shown in FIG. 1B.

Turning to FIGS. 1B-1D, the fabric covering 21 may be provided around the annular ring 18, the skirt 30, the rail ring 52, and the flexible core 60. As shown, the fabric covering 21 may be a single piece of tubular fabric, e.g., Dacron or other polyester fabric, that may be wrapped around the components of the gasket member 12, with any loose ends or edges 71 of the fabric secured together, e.g., by sutures 72, and/or by adhesives, other connectors (not shown), and the like. Alternatively, multiple pieces of fabric may be used, if desired. Optionally, the fabric covering 21 may be fixed relative to one or more locations of the components of the gasket member 12 (e.g., the annular member 18, the flexible core 60, and/or the skirt 30), e.g., by one or more sutures delivered through the fabric covering 21 and/or one or more openings in the components (not shown).

Because the fingers 82 of the skirt 30 are biased or otherwise flared outwardly, the fingers 82 may direct the fabric covering 21 radially outwardly away from the annular ring 18, e.g., adjacent the lower edge. Thereafter, the fabric covering 21 and fingers 82 may be compressed inwardly, e.g., towards or against the annular ring 18. When such compressive force is released, however, the fingers 82 may resiliently return outwardly, thereby directing the fabric covering 21 outwardly. This feature may enhance a seal between the fabric covering 21 and surrounding tissue without applying substantial force on the contacted tissue.

Optionally, the gasket member 12 may include one or more additional components. For example, as shown in FIGS. 1B-1D, the gasket member 12 may include a collar or stand-off 58 that extends upwardly from the annular ring 18 and/or sewing cuff 20, e.g., for receiving a valve member (not shown), as described further elsewhere herein. The collar 58 may be attached to or otherwise extend upwardly from the annular ring 18 and/or the sewing cuff 20, e.g., to enhance a seal between the gasket member 18 and a prosthetic valve.

Referring to FIGS. 4A-4C, the collar 58 may include a core 40, which may be separate from the core 60 of the sewing cuff 20. The core 40 of the collar 58 and the core 60 of the sewing cuff 20 may be attached to one another, e.g., by bonding, fusing, interference fit, and the like, and/or may be maintained adjacent one another by the surrounding fabric. Alternatively, the core 40 of the collar 58 and the core 60 of the sewing cuff 20 may be formed as a unitary piece, e.g., by molding, cutting and/or machining from a blank, and the like. In a further alternative, the collar 58, including the core 40 and the surrounding fabric 37, may be disposed adjacent the sewing cuff 20 and/or annular ring 18, and attached thereto, e.g., using one or more sutures or other connectors (not shown).

The material of the core 40 of the collar 58 may be substantially flexible, e.g., manufactured in a desired annular shape, yet easily deformed, e.g., deflected, stretched, and/or compressed. Exemplary materials for the core 40 of the collar 58 include plastic, such as PET, silicone or other elastomeric materials, foam, fabric, felt, polymers, and the like, e.g. similar to the core 60 of the sewing cuff 20. The materials may be molded or otherwise formed into the core 40, e.g., using known molding, extrusion, cutting, machining, or other manufacturing procedures.

In one embodiment, shown in FIG. 4C, the core 40 of the collar 58 may be cut from a flat sheet of base material, for example, by laser cutting, mechanical cutting, and the like. Thus, the core 40 of the collar 58 may initially be formed as a long band of material. The band for the core 40 may have an undulating shape, e.g., corresponding to the multiple-lobular shape of the core 60 of the sewing cuff 20, for example, including three alternating peaks and valleys. Alternatively, the band may be substantially straight if the surface of the core 60 of the sewing cuff 20 is substantially planar. The band may be wrapped around a mandrel or otherwise restrained in a generally cylindrical shape with the ends adjacent to one another. For example, ends 40a of the band may be attached together using fasteners, such as sutures, clips, adhesive and the like, to maintain the generally cylindrical shape and create the core 40 of the collar 58. Alternatively, the band may be heat treated or otherwise processed to program the generally cylindrical shape to create the core 40 of the collar 58. The generally cylindrical shape may include the ends overlapping one another, spaced apart from one another to provide an open "C" shape, and/or attached to one another.

After forming the core 40 of the collar 58 into the generally cylindrical shape, the core 40 of the collar 58 may be covered with fabric 37, as shown in FIGS. 4A and 4B. The fabric 37 may be shaped to provide a flexible skirt 42 around at least a portion of the collar 58, as shown in FIG. 4B. For example, the fabric may be folded over on itself to provide a skirt 42 defined by a double thickness of fabric that extends from the collar 58. The skirt 42 may be free to move and/or conform, e.g., when the collar 58 is secured to the gasket member 12, as described further below. Alternatively, the skirt 42 may be defined by a single layer of fabric and/or other flexible material (not shown) attached to or otherwise extending from the collar 58 and/or the fabric 37.

The skirt 42 may be sufficiently large such that sutures or fasteners (not shown) may be received through both the skirt 42 and the cuff 20. When the collar 58 is directed into contact with the gasket member 12, as shown in FIGS. 1B-1D, the skirt 42 is disposed at the bottom of the collar 58 so that the skirt 42 may directly contact the gasket member 12. To attach the collar 58 to the sewing cuff 20, sutures (not shown) may be threaded through the skirt 42, e.g., through holes 40b in the core 40 (shown in FIG. 4C), and into the fabric 21 covering the sewing cuff 20. Alternatively or additionally, other fasteners such as clips, adhesive, and the like may be used in place of, or in addition to, the sutures.

Many features of the gasket member 12 may be similar to the devices disclosed in U.S. Publication Nos. US 2004/0122516, filed as Ser. No. 10/327,821 on Dec. 20, 2002, US 2005/0165479 filed as Ser. No. 10/765,725 on Jan. 26, 2004, US 2006/0276888 filed as Ser. No. 11/144,254 on Jun. 3, 2005, US 2006/0235508, filed as Ser. No. 11/279,246 on Apr. 10, 2006, US 2007/0260305, filed as Ser. No. 11/742,390 on Apr. 30, 2007, US 2007/0265701, filed as Ser. No. 11/742,459 on Apr. 30, 2007, US 2007/0150053, filed as Ser. No. 11/567,735 on Dec. 7, 2006 and US 2007/0016285 filed as Ser. No. 11/420,720 on May 26, 2006, the entire disclosures of which are expressly incorporated by reference herein, and US 2006/0195184 incorporated by reference above. Optionally, the gasket member 12 may include other additional features, such as the guide shields disclosed in Publication No. US 2007/0260305, filed as application Ser. No. 11/742, 390 on Apr. 30, 2007, the entire disclosure of which is also expressly incorporated by reference herein.

To make a gasket member, such as the gasket member 12 shown in FIGS. 1A-1D, the following procedure may be used. Although the steps or stages of manufacturing and assembly are described below in an exemplary order, it will be appreciated that the order of individual steps may be changed for convenience, efficiency, and/or other reasons.

Initially, as described above, the components of the gasket member 12 may be formed. For example, the band for the annular ring 18 may be formed from a sheet of Nitinol or other material, the bands for the skirt 30 and core 40 of the collar 58, and the rail ring 52 and guide rails 50 may be formed from a sheet of PET or other material, and the core 60, commissure supports 68, and stress diffusors 55 for the sewing cuff 20 may be formed, e.g., from silicone or other material, e.g., using the materials and methods described above.

The skirt 30 may be attached to the band for the annular ring 18, e.g., by directing and tying sutures 84 through corresponding holes 80a, 18a in the skirt 30 and band 18, as shown in FIG. 2E and described above. The skirt 30 and band 18 may be rolled, and the ends 80b of the skirt 30 may be attached together, e.g., by directing and tying sutures (not shown) through holes in the ends 80b, to create the annular ring 18, as shown in FIG. 2F.

The first ends 51a of the guide rails 50 may be bent upwardly relative to the rail ring 52, as shown in FIG. 3A, and the core 60 of the sewing cuff 20 may be placed over the rail ring 52, as shown in FIG. 1B, with the guide rails 50 aligned with the holes 64 in the core 60. The guide rails 50 may be directed through respective holes 64, as shown in FIG. 3C, and then the stress diffusors 55 may be secured to the core 60 and rail ring 52, as shown in FIG. 3F. Thus, the rail ring 52 and core 60 may be maintained relative to one another, while having some freedom to move relative to one another. Optionally, commissure supports 68 may be attached to the core 60 adjacent respective holes 64, e.g., before or after directing the guide rails 50 through the holes and/or attaching the stress diffusors 55.

Tabs 56 on the rail ring 52 may be bent downwardly, and sutures 59 may be directed through respective sets of holes 56a, 18b in the tabs 56 and annular ring 18, similar to the exemplary suture 59 shown in FIG. 1B. As a result, the core 60, rail ring 52, annular ring 18, and skirt 50 may be attached into an assembly. The assembly may be received within or substantially covered with the fabric covering 21. This may involve creating openings in the fabric covering 21 to accommodate receiving the guide rails 50 therethrough, while the other components are substantially captured within the fabric covering 21, as best seen in FIG. 1A.

The collar 58 may be assembled by covering the core 40 with fabric 37, as shown in FIGS. 4A-4C. The collar 58 may then be attached to the covered assembly, e.g., to the sewing cuff 20. For example, sutures may be directed through holes in the core 40 and/or the fabric 37, and the fabric covering 21 of the covered assembly over the sewing cuff 20. Any excess fabric, knots, or loose suture ends may be cut or removed, as desired, resulting in the fully assembled gasket member 12 shown in FIG. 1A.

Figure 7A:
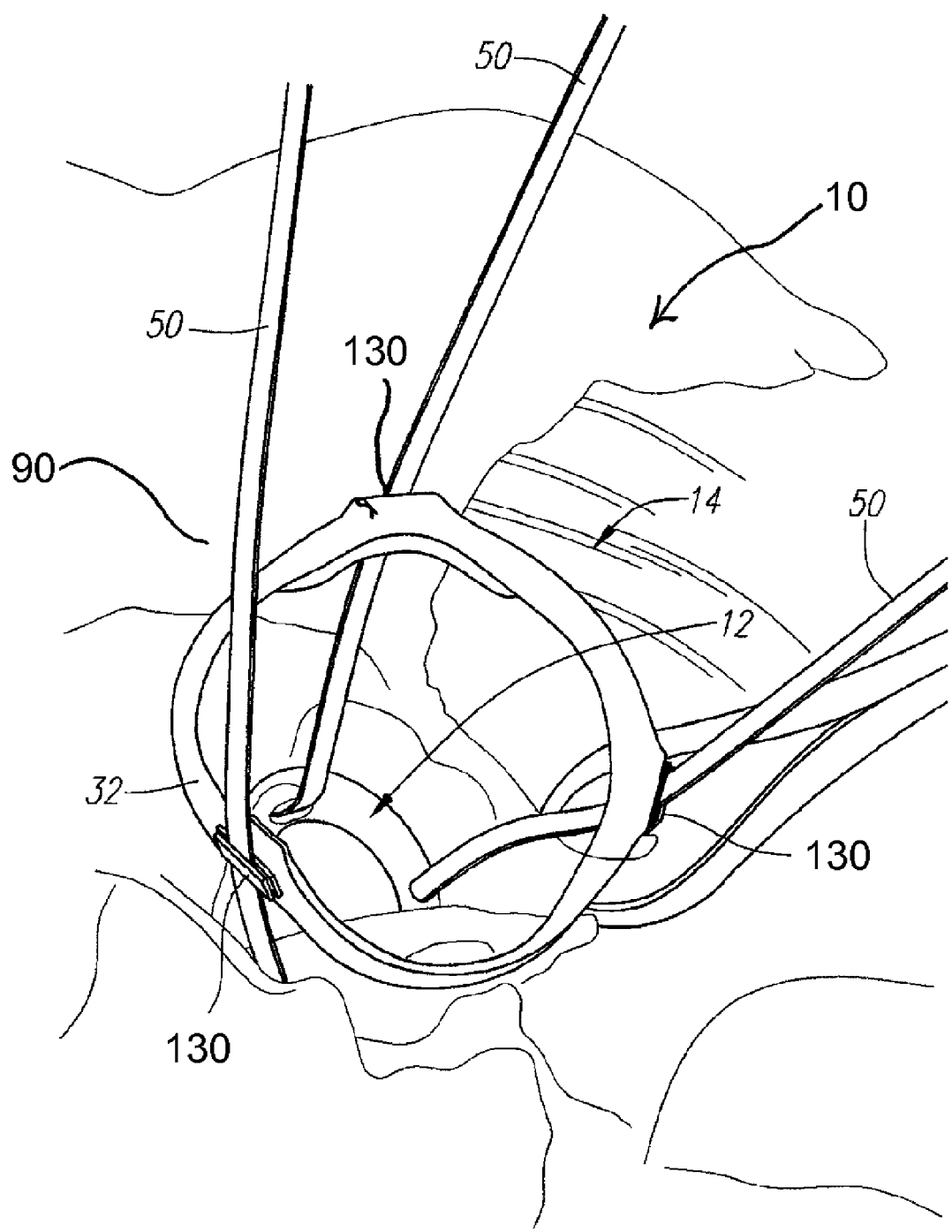
FIGS. 7A and 7B are perspective views of a biological annulus, showing a method for implanting the gasket member of FIG. 1B and the valve member of FIG. 5 within the biological annulus.
Figure 7B:
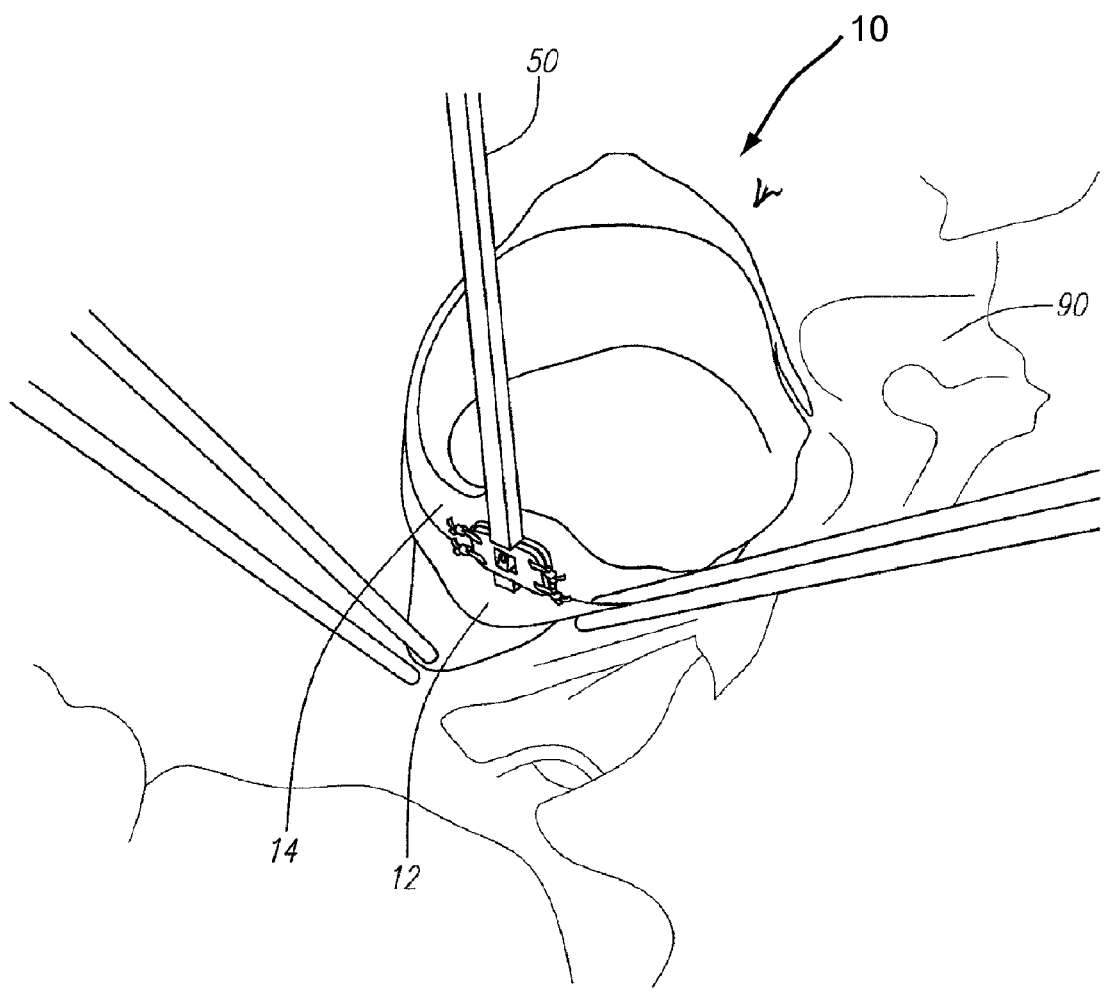

The gasket member 12 discussed above may be combined with a valve member 14 to provide a heart valve assembly 10, e.g., as shown in FIGS. 7A and 7B, and discussed further below. An exemplary embodiment of a valve member 14 is depicted generally in FIG. 5, although leaflets or other valve elements of the valve member 14 have been omitted for clarity. The valve member 14 generally includes an annular shaped body or frame 32 and one or more valve elements (not shown) that open and close to allow fluid flow through the valve member 14. The valve member 14 may include a fabric covering 35, e.g., similar to that of the gasket member 12, e.g., covering the frame 32 and/or other components of the valve member 14. The frame 32 may have a noncircular, e.g., multiple lobular shape corresponding to a shape of the biological annulus within which the valve member 14 is to be implanted. For example, the valve member 14 may have a tri-lobular shape, including three lobes separated by cusps or scallops, e.g., corresponding to a sinus of Valsalva above an aortic valve site. In one embodiment, the valve member 14 may be a bioprosthetic valve member, e.g., an annular frame 32 carrying a plurality of tissue leaflets (not shown). The frame 32 may include a plurality of struts (also not shown for clarity) that may be attached to and/or otherwise carry the leaflets. For example, the struts may include a laminate structure, including two or more sheets of flexible material, similar to the valves disclosed in U.S. Pat. No. 6,371,983, the entire disclosure of which is expressly incorporated by reference herein, and U.S. Publication No. US 2006/0276888, incorporated by reference above.

Alternatively, the valve member 14 may be a connecting device to which a valve (not shown) may be connected or that may otherwise receive a valve component, such as the connection adapter elements shown in U.S. Publication No. US 2005/0043760, filed as Ser. No. 10/646,639 on Aug. 22, 2003, the entire disclosure of which is expressly incorporated by reference herein. In another alternative, the valve member 14 may include a mechanical valve or other valve (not shown), such as those disclosed in US 2005/0165479 and US 2007/0016285, incorporated by reference above.

Figure 6A:
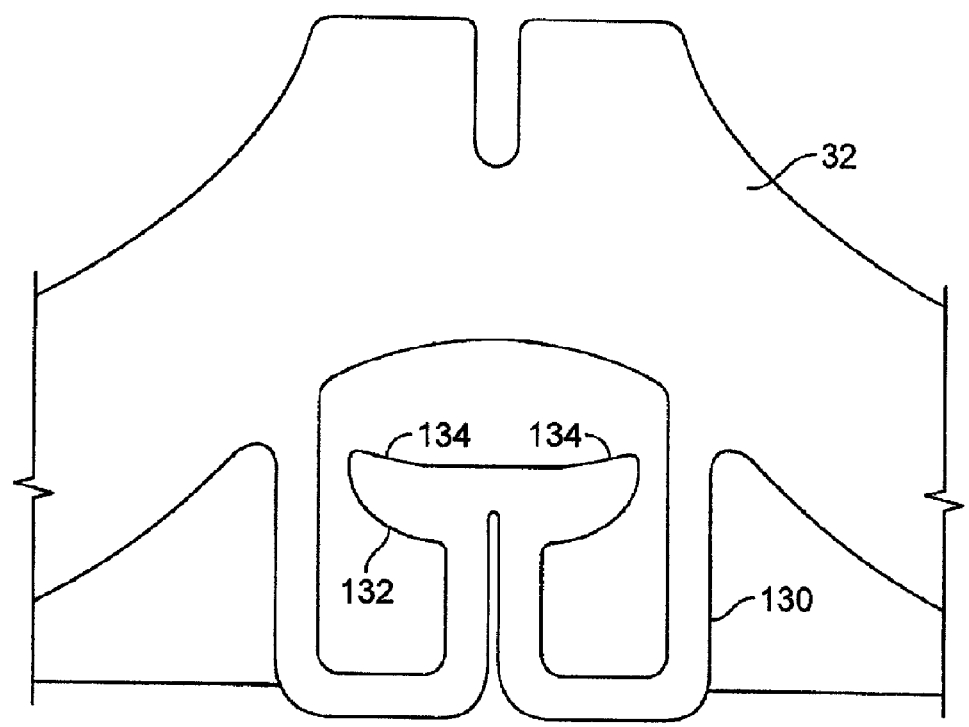
FIGS. 6A and 6B are detailed views of another embodiment of a receptacle that may be provided on the valve member of FIG. 5 and including a cantilever spring and detents defining a track for receiving a guide rail therein.
Figure 6B:
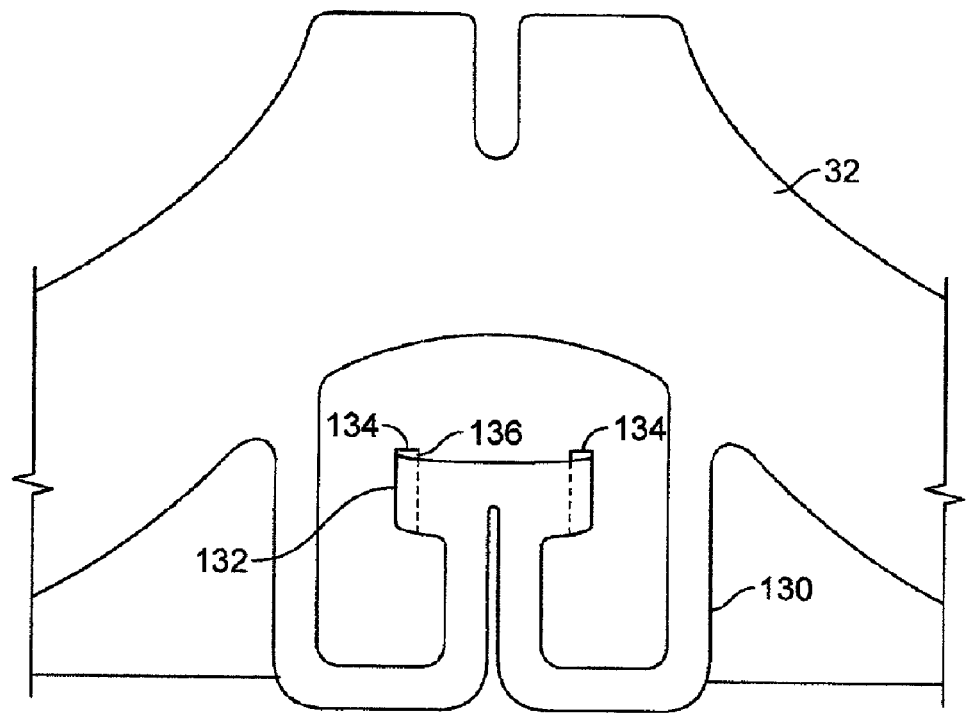

The frame 32 of the valve member 14 may include a plurality of receptacles or other features 130 configured to receive the guide rails 50 therethrough. An exemplary embodiment of a receptacle 130 formed with the frame 32 is shown in more detail in FIGS. 6A-6E. Each receptacle 130 may include a cantilever spring 132 including a first end supported by the valve frame 32 and a second free end including one or more detents 134. As shown in FIGS. 6A and 6B, the detents 134 may be bent or otherwise formed to at least partially define a track, slot, or other passage 136 for receiving a guide rail 50 therethrough. The receptacle 130 may be formed integrally with the valve frame 32, e.g., laser cut or otherwise formed from a Nitinol or other sheet used to make the frame 32. Alternatively, other receptacles or connectors may be provided on the valve member 14. Exemplary valves and receptacles are disclosed in U.S. Publication No. US 2007/0265701, incorporated by reference above.

Turning to FIGS. 7A and 7B, a method is shown for implanting a prosthetic heart valve assembly 10 into a biological annulus. Generally, the heart valve assembly 10 includes a gasket member 12 and a valve member 14, such as those shown in FIGS. 1A and 5, respectively, and/or as described elsewhere herein or in the applications incorporated by reference herein. The biological annulus 90 may be the site for replacing an existing natural or previously implanted heart valve, such as a tricuspid, mitral, aortic, or pulmonary valve within a patient's heart (not shown).

Figure 5:
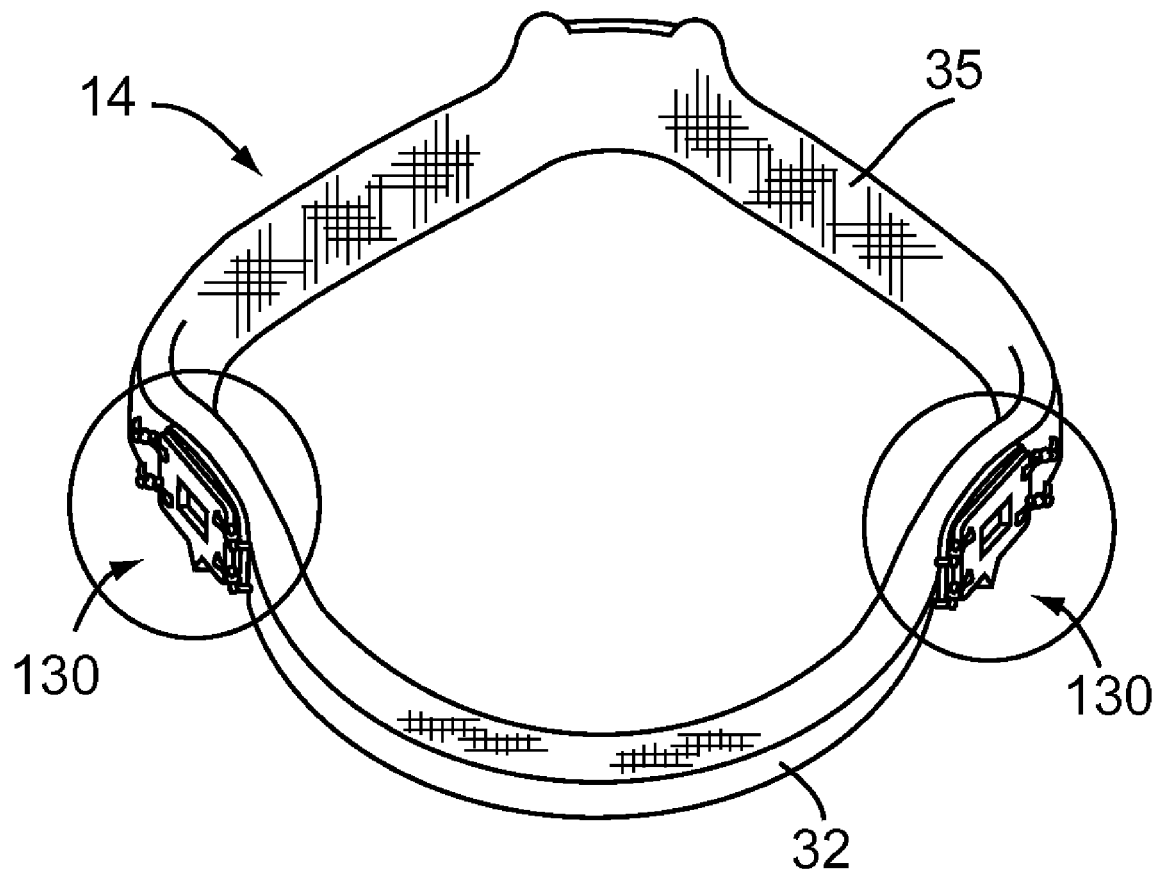
FIG. 5 is a perspective view of an exemplary embodiment of a valve member for a two piece heart valve assembly including receptacles for receiving guide rails and with leaflets removed for clarity.

Before implanting the heart valve assembly of FIGS. 1B and 5, the patient may be prepared for the procedure using known methods. For example, the patient may be placed on cardiopulmonary bypass (CPB), and the patient's heart may be exposed, e.g., by sternotomy, thoracotomy, or other open or minimally invasive procedure. An incision may be created in the blood vessel above the valve being replaced (not shown), e.g., in the aorta for an aortic valve replacement, in order to access the annulus 90. The existing natural or prosthetic heart valve and/or leaflets (also not shown) may then be removed from the annulus 90 using known methods.

A gasket member 12 and a valve member 14 may be selected based upon the anatomy encountered, e.g., having a plurality of lobes matching the lobes of the biological annulus 90 and/or having a cross-sectional dimension corresponding to the interior cross-section of the biological annulus 90. For example, one or more valve sizer tools (not shown) may be introduced into the biological annulus 90 to facilitate identifying an appropriate sized valve assembly 10 to be implanted. Optionally, a gasket member 12 and/or valve member 14 may be selected having a size that is larger than the biological annulus 90. For example, the gasket member 12 may have a diameter in its relaxed condition that is slightly larger than the biological annulus 90, e.g., such that the gasket member 12 may at least partially reshape and/or dilate the biological annulus 90 upon implantation. In addition or alternatively, the valve member 14 may have a diameter or other cross-section that is substantially larger than the biological annulus 90, e.g., for supra-annular or intra-sinus implantation, which may accommodate the larger size.

With reference to FIG. 7A, the gasket member 12 may be introduced into the patient until the annular ring 18 (not shown in FIG. 7A) is disposed within the biological annulus 90. In one embodiment, the gasket member 12 may be restrained in a contracted condition by tensioning guide rails 50, e.g., with a delivery tool (not shown), and introduced into the patient's body until the annular ring 18 extends at least partially into the biological annulus 90. The gasket member 12 may then be expanded or at least partially released within the biological annulus 90, e.g., to reshape and/or dilate the biological annulus 90 or otherwise direct the surrounding tissue outwardly. Once stabilized, the guide rails 50 may be released entirely from the delivery tool (not shown). Optionally, a dilation tool (not shown) may be advanced into the gasket member 12 and expanded to forcibly (e.g., plastically) expand the annular ring 18 within the biological annulus 90.

In an alternative embodiment, a tool (not shown) may be used to maintain the gasket member 12 in the contracted condition, and the gasket member 12 may be released once the annular ring 18 is positioned within the biological annulus 90, whereupon the gasket member 12 may resiliently expand, e.g., to contact and/or dilate tissue surrounding the annulus 90. Such a delivery tool may also constrain or limit movement of the guide rails 50 during delivery of the gasket member 12, e.g., to keep the guide rails 50 substantially out of the field of view. Exemplary apparatus and methods for delivering the gasket member 12 are disclosed in U.S. Publication Nos. US 2007/0225801, filed as Ser. No. 11/685,192 on Mar. 12, 2007, US 2007/0260305, filed as Ser. No. 11/742,390 on Apr. 30, 2007, and US 2007/0265701, filed as Ser. No. 11/742,459 on Apr. 30, 2007, the entire disclosures of which are expressly incorporated by reference herein.

With the gasket member 12 deployed within the biological annulus 90, the sewing cuff 20 (not shown in FIGS. 7A and 7B) may contact the tissue surrounding the supra-annular space above the biological annulus 90. One or more fasteners, e.g., clips or sutures (not shown), may be directed through the gasket member 12 into the tissue above and/or surrounding the biological annulus 90. Exemplary fasteners and methods for using them to secure the gasket member 12 may be found in U.S. Publication Nos. US 2004/0122516, filed as Ser. No. 10/327,821 on Dec. 20, 2002, US 2005/0043760, filed as Ser. No. 10/646,639 on Aug. 22, 2003, US 2005/0080454 filed as Ser. No. 10/681,700 on Oct. 8, 2003, and US 2006/0122634, filed as Ser. No. 11/004,445 on Dec. 3, 2004, the entire disclosures of which are expressly incorporated by reference herein.

With the gasket member 12 within the biological annulus 90, the valve member 14 may then be advanced into the patient's body towards the biological annulus 90. In the embodiment shown, the valve member 14 may be advanced along the guide rails 50 toward the gasket member 12. Before advancing the valve member 14, the guide rails 50 may be released and removed completely from any delivery tool (not shown) if used to deliver the gasket member 12. After releasing the guide rails 50 from the delivery tool, the receptacles 130 of the valve member 14 may be aligned with the free ends 51b of the guide rails 50 protruding from the annulus 90 and/or the patient's body. Thus, the guide rails 50 may be passed upwards through the receptacles 130, so that the valve member 14 is moving towards the gasket 12 along the rails 50. Optionally, the valve member 14 may include guides or other features (not shown) to facilitate loading the ends 51b of the guide rails 50 into the receptacles 130. For example, the fabric (not shown) covering the valve member 14 may include a slot or other opening that may receive the free ends 51b of the guide rails 50, and direct the guide rails 50 into the receptacles 130. In addition or alternatively, visual markers may be provided on the valve member 14, e.g., above or around the receptacles 130, to facilitate inserting the guide rails 50 through the receptacles 130.

Figure 6C:
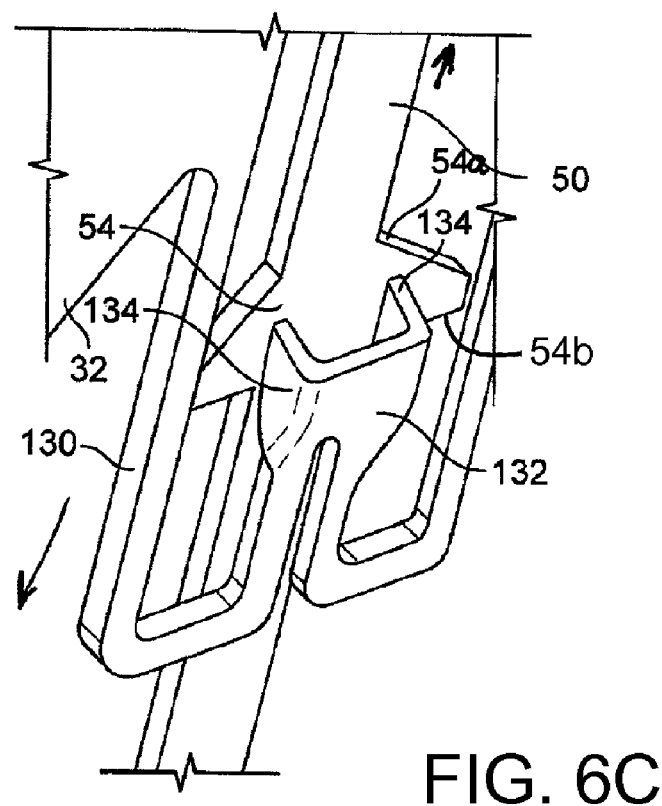
FIGS. 6C and 6D are perspective and side detail views, respectively, of the receptacle of FIGS. 6A and 6B receiving a guide rail therethrough, the detents on the cantilever spring causing the cantilever spring to deflect outwardly to accommodate retention elements on the guide rail passing through the receptacle.
Figure 6D:
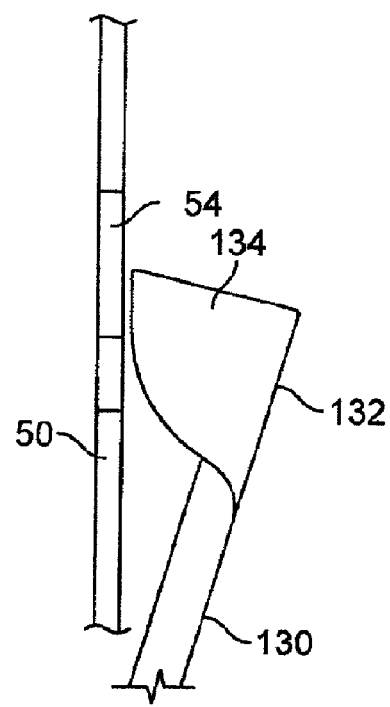
Figure 6E:
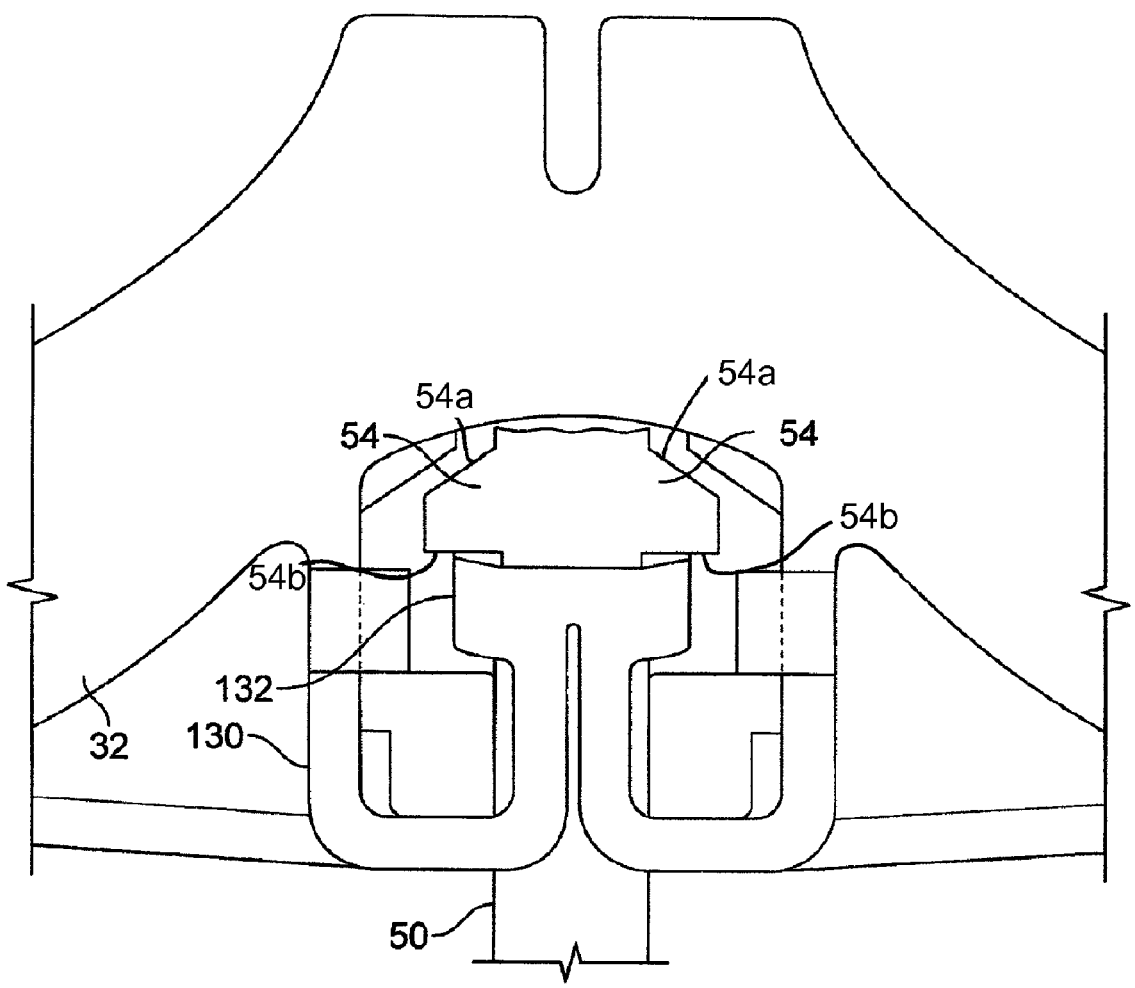
FIG. 6E is a detailed view of the receptacle of FIGS. 6A-6D with the retention elements of a guide rail engaged with the detents of the receptacle and a top portion of the guide rail severed and removed.

With the guide rails 50 received through the receptacles 130 of the valve member 14, the valve member 14 may be advanced distally over the guide rails 50 towards the gasket member 12 until the valve member 14 engages or otherwise contacts the gasket member 12. Optionally, the valve member 14 may be delivered using a valve holder or other delivery tool (not shown) and/or using methods, such as those disclosed in Publication No. US 2007/0288089, filed as application Ser. No. 11/742,481 filed Apr. 30, 2007, the entire disclosure of which is expressly incorporated by reference herein. The valve member 14 may be advanced until the receptacles 130 securely engage with retention elements 54, e.g., until the distal edges 54b of the retention elements 54 are disposed above the detents 134 of the receptacles 130. This process is depicted in FIGS. 6C-6E. When the valve member 14 is disposed immediately adjacent the gasket member (not shown in FIGS. 6C-6E, see FIGS. 7A and 7B), the retention elements 54 on the guide rails 50 may encounter the detents 134 on the cantilever spring 132.

As shown in FIGS. 6C-6E, the retention elements 54 may include tapered upper edges 54a and the detents 134 may include tapered lower edges. Thus, as the valve member 14 is directed downwardly, the tapered edges may slide relative to one another, causing the cantilever spring 132 to deflect resiliently outwardly, as shown in FIGS. 6C and 6D. Once the detents 134 pass below the retention elements 54, the cantilever spring 132 may return inwardly, thereby capturing the detents 134 below the retention elements 54. The detents 134 may include substantially blunt upper edges and the retention elements 54 may include substantially blunt lower edges 54b, thereby preventing the valve member 14 from being withdrawn back over the retention elements 54. Thus, the retention elements 54 may allow unidirectional advancement of the valve member 14, i.e., towards the gasket member 12.

To facilitate the connection between the valve member 14 and the gasket member 12, the user may pull or otherwise subject the guide rails 50 to proximal tension, while advancing the valve member 14 until a "click" or other audible and/or tactile feedback is provided that confirms that the detents 134 and retention elements 54 are engaged. Each set of detents 134 and retention elements 54 may be engaged sequentially or simultaneously. Consequently, as shown in FIG. 7B, the valve member 14 is securely positioned relative to gasket member 12, with the retention elements 54 (shown in FIG. 6E) preventing the valve member 14 from being moved away from the gasket member 12.

In an exemplary embodiment, the retention elements 54 may be disposed a predetermined distance from the first ends 51a of the guide rails 50, thereby securing the valve member 14 against or immediately adjacent the gasket member 12. The predetermined distance may be set such that the frame 32 of the valve member 14 substantially contacts the sewing cuff 20, e.g., to at least partially compress the core 60, which may enhance sealing between the valve member 14 and the gasket member 12. In addition, the valve member 14 may be received within the collar 58, which may also enhance a seal between the valve member 14 and gasket member 12.

Turning to FIG. 6E, the excess portions of the guide rails 50 above the receptacles 130 may then be removed. For example, the free ends 51b of the guide rails 50 may be pulled with sufficient tensile force to break at the weakened regions on the guide rails 50. Alternatively, the guide rails 50 may simply be cut or otherwise severed above the retention elements 54.

It will be appreciated that elements or components shown with any embodiment herein are exemplary for the specific embodiment and may be used on or in combination with other embodiments disclosed herein. For example, receptacles and/or guide rails may provided on any of the embodiments described herein, whether shown in the drawings in that combination. Optionally, if receptacles and retention elements are provided on the valve and gasket members described herein, retention elements on the guide rails may be eliminated if the guide rails are used only for guidance and the receptacles and retention elements are provided for securing the valve relative to the gasket member.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A prosthesis for receiving a prosthetic valve to replace a preexisting natural or prosthetic heart valve within a biological annulus, comprising:
    an annular member sized to be received within a biological annulus;
    a sewing cuff extending outwardly from the annular member above a plane of the annular member;
    a rail ring disposed adjacent the annular member within a fabric covering covering the annular member and the rail ring;
    a plurality of guide rails extending from the rail ring transversely relative to a plane defined by the rail ring, the guide rails extending from the rail ring through respective openings in the fabric covering; and
    a collar attached along its length to an outer surface of the fabric covering along an inner surface of the sewing cuff above the plane defined by the rail ring.

2. The prosthesis of claim 1, wherein each of the guide rails comprises one or more retention elements for securing a prosthetic valve relative to the prosthesis.

3. The prosthesis of claim 1, further comprising a flexible core disposed adjacent the rail ring, opposite the annular member, the flexible core covered with the fabric covering to at least partially define the sewing cuff extending outwardly from the annular member.

4. The prosthesis of claim 3, wherein the annular member, the rail ring, and the flexible core are aligned concentrically with one another such that, when covered by the fabric covering, a fluid flow passage is defined through the prosthesis.

5. The prosthesis of claim 1, wherein the collar comprises a core that is covered with a fabric.

6. The prosthesis of claim 5, wherein the collar further comprises a flexible skirt extending therefrom that engages the sewing cuff.

7. A prosthesis for receiving a prosthetic valve to replace a preexisting natural or prosthetic heart valve within a biological annulus, comprising:
    an annular member sized to be received within a biological annulus;
    a sewing cuff extending outwardly from the annular member above a plane of the annular member;
    an annular skirt extending outwardly from the annular member below the annular member;
    a collar attached along its length to an inner surface of the sewing cuff;
    a rail ring disposed between the sewing cuff and the annular member generally within a plane above the plane defined by the annular member and within a fabric covering the annular member and the rail ring; and
    a plurality of guide rails extending from the rail ring transversely relative to the plane through respective openings in the fabric covering.

8. The prosthesis of claim 7, wherein the rail ring comprises tabs connecting the rail ring to the annular member by sutures extending between the tabs and the annular member.

9. The prosthesis of claim 7, and further comprising a flexible core within the sewing cuff, wherein the rail ring is disposed below the flexible core and second ends of the guide rails pass through respective openings in the flexible core so that the second ends of the guide rails extend above the plane of the rail ring.

10. The prosthesis of claim 7, wherein the collar comprises a core that is covered with a fabric.

11. The prosthesis of claim 10, wherein the collar further comprises a flexible skirt extending therefrom that engages the sewing cuff.

* * * * *